US005935170A

United States Patent [19]

Håkansson et al.

[11] Patent Number: 5,935,170

[45] **Date of Patent: *Aug. 10, 1999**

[54] DISCONNECTION DEVICE FOR IMPLANT COUPLING AT HEARING AIDS

[75] Inventors: Bo Håkansson, Göteborg; Peder Carlsson, Kungälv, both of Sweden

[73] Assignee: P & B Research AB, Gothenburg, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/941,492

[22] Filed: Sep. 30, 1997

Related U.S. Application Data

[63] Continuation of application No. 08/566,043, Dec. 1, 1995, abandoned.

[30] Foreign Application Priority Data

Dec. 2, 1994 [SE] Sweden ................................ 9404189

[51] Int. Cl.$^{6}$ ........................................ A61F 2/28

[52] U.S. Cl. ........................ 623/16; 600/25; 403/343; 403/348; 411/339; 411/509; 24/590

[58] Field of Search ........................ 606/73; 403/348, 403/343; 24/590, 297; 411/338, 339, 509, 508, 913; 623/10, 16; 600/25

[56] References Cited

U.S. PATENT DOCUMENTS

| | | | |
|---|---|---|---|
| 2,367,458 | 1/1945 | Coplen | 403/348 |
| 3,034,798 | 5/1962 | Portz | 403/343 X |
| 4,486,918 | 12/1984 | Peebles | 403/348 X |
| 4,494,555 | 1/1985 | Abrioux et al. | 403/348 X |
| 4,506,419 | 3/1985 | Mitomi | 411/508 X |
| 5,193,961 | 3/1993 | Hoyle et al. | 411/508 X |

FOREIGN PATENT DOCUMENTS 0 715 839 A2 6/1996 European Pat. Off. .

*Primary Examiner*—David H. Willse
*Attorney, Agent, or Firm*—Woodbridge & Associates

[57] ABSTRACT

A device for disconnection of a connecting device between an implant (2) and a device (12) connectable thereto, which coupling device is of the type incorporating a first and a second coupling part (6 and 11, resp.), one of which parts (11) in coupling position being elastically retained in a recess provided in the other one of the parts (6), said recess having a depth permitting the second coupling part to project into it to coupling position and where the coupling parts (6, 11) in coupling position are arranged with mutual end-to-end contact and substantially in the axial extension of each other, thus that they are mutually rotatable about a substantially common axis, whereby at least one of the coupling parts (6, 11) is provided with at least one member (19), which together with the other coupling part (11, 6) in at least one mutual rotational position for the two coupling parts, have a total added axial longitudinal measure, which gives the part introduced in the recess a clearance to the other coupling part in interconnected position, and which together with the other coupling part in at least one other mutual rotational position have an overall added axial longitudinal measure, which does not permit the coupling parts to be interconnected, whereby the coupling parts without axial influence upon the implant are brought apart during the mutual rotation of the coupling parts to said at least one other mutual rotational position.

16 Claims, 4 Drawing Sheets

DISCONNECTION DEVICE FOR IMPLANT COUPLING AT HEARING AIDS

Figure 1:
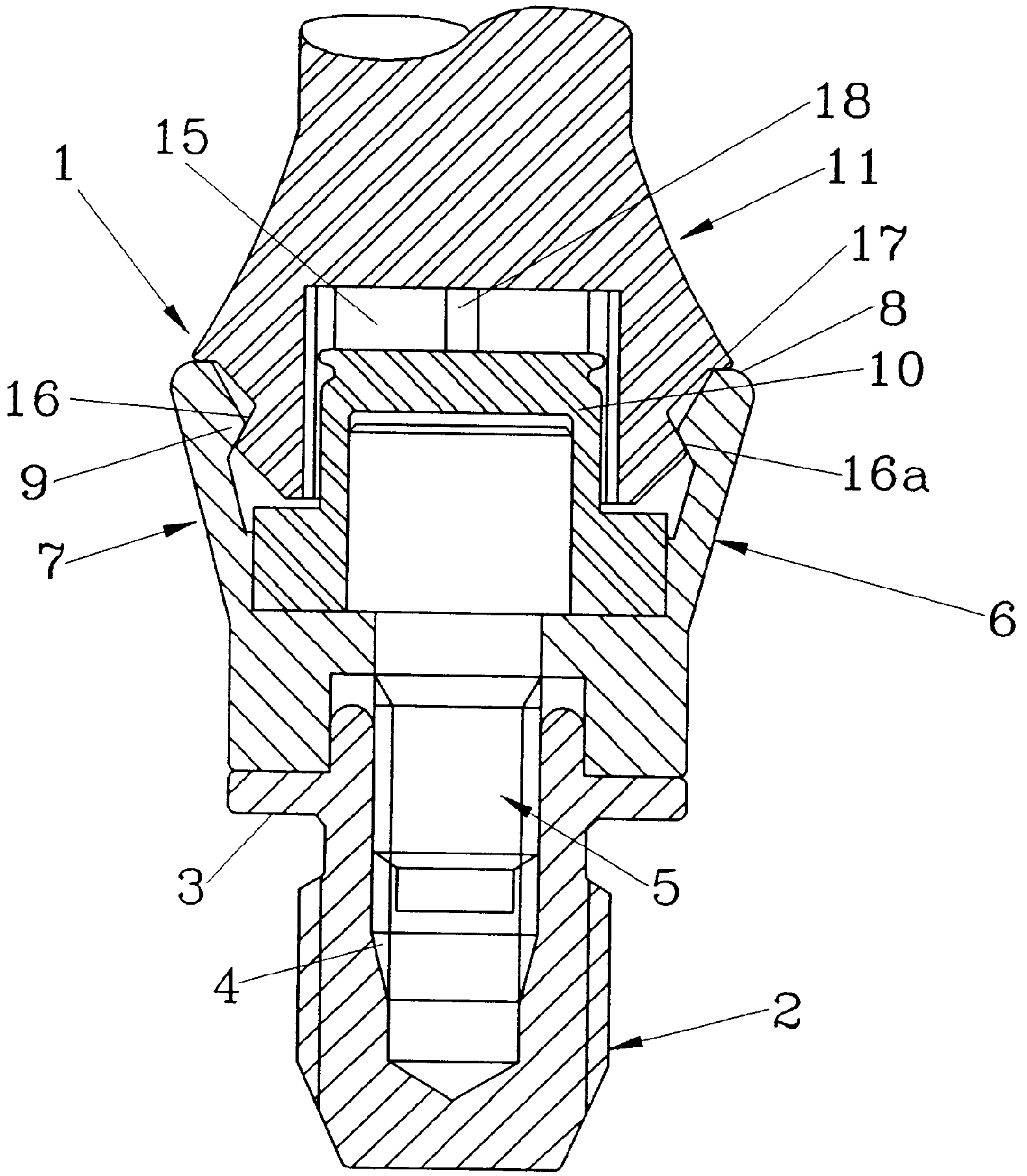

This application is a continuation of application Ser. No. 08/566,043, filed Dec. 1, 1995, now abandoned.

The present invention refers to a disconnection device at hearing aids of the type, which is connected to an implant anchored in the skull bone of a person with impaired hearing, wherein the implant constitutes or supports a first coupling member intended for connection to a second coupling part, which is provided on a vibration exciting apparatus, said coupling parts being constituted by a substantially cup-shaped female part and a male part, which is insertable therein under mutual flexing.

Such skull bone anchored implants are often made as a metal fixture, in which a first coupling part is arrestable. To this first coupling part, which thus is arrestable in the fixture, is connectable a second coupling part cooperating therewith and being connected to the vibration exciting part of the hearing aid.

In known embodiments the coupling parts often have been made as a female coupling part and a male coupling part, wherein the male part usually has been made as an, at least partially ball-shaped body, whereas the female part has been constituted by a cup-shaped body, the wall of which has been made sufficiently elastic to permit the male part to be snapped-in, in that its edge portion has been made sufficiently thin, or more often, has been provided with axially extending slots. In another embodiment the coupling parts have been designed as a bayonet coupling.

In all these cases one of the coupling parts has been designed as a form stiff body, whereas the other part has been designed to be able to flex, or has been provided with flexing means for making it possible to effect manual interconnection and disconnection of the coupling parts. However, this resiliency must not be to soft, in order to ascertain a safe signal transferring contact between the opposed metallic surfaces, which engage each other and a secure retention of the interconnected parts of the coupling also at possible impacts against the protruding, vibration exciting apparatus. Simultaneously this means, that the force, which must be used at connection as well as at disconnection will become rather big, which might make it difficult for the bearer of the apparatus to manage this in a simple manner, and as the force also must be applied in the longitudinal direction of the implant, there is also an increased risk that the implant shall be subjected to such pulling forces and bending moments at disconnection, that the retention of the implant in the skull bone is impaired or even jeopardized. Furthermore from a psychological aspect it is uninviting to pull outwards, as the bearer gets the feeling that the entire implant might come loose from the skull bone.

The purpose of the present invention is to provide a device of the type described in the introduction, by which the above mentioned drawbacks are eliminated, and this has been obtained by the features defined in the accompanying claims.

Hereinafter the invention will be further described with reference to an embodiment shown in the accompanying drawings.

Figure 2:
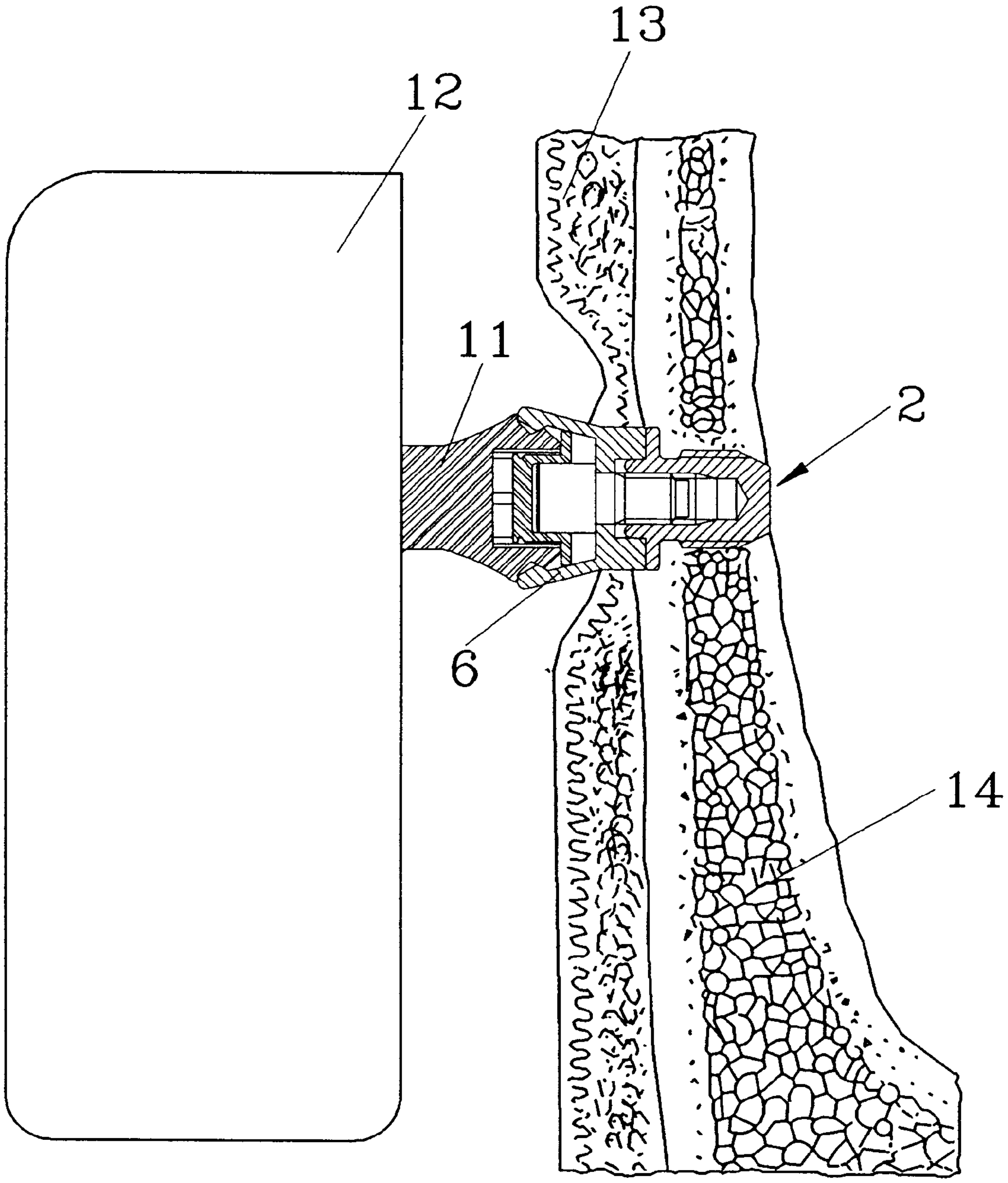
Figure 3:
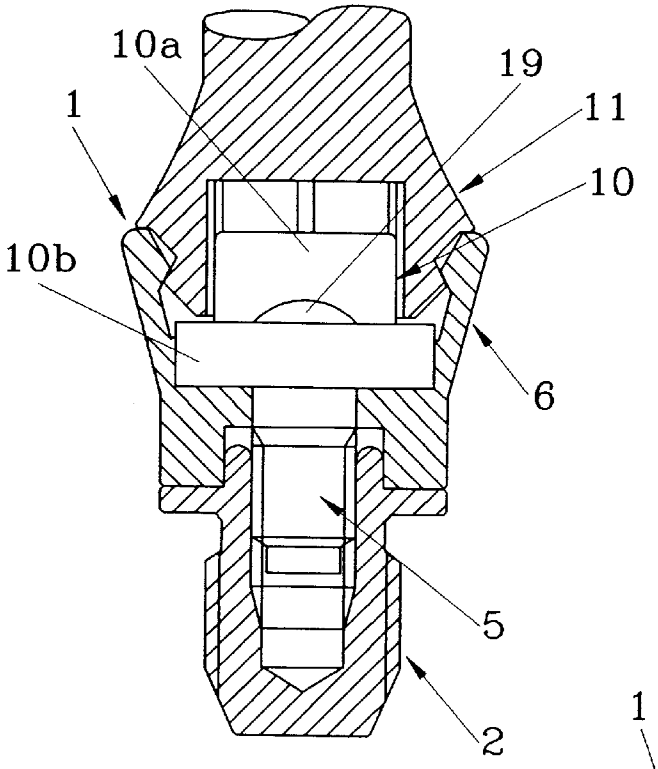
Figure 4:
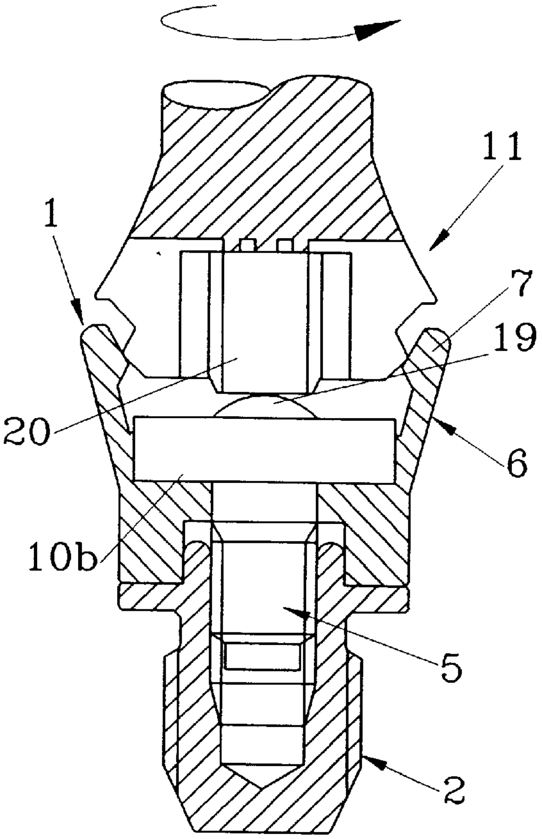

FIG. 1 shows in a cross section and in coupling position a type of coupling device, which preferably is provided with a disconnection device according to the invention, FIG. 2 is an illustration, partially in section, of a coupling device according to FIG. 1 implanted in a skull bone and with a hearing aid connected thereto, FIG. 3 shows in a view corresponding to FIG. 1 the same coupling position, but with a covering washer forming part of the disconnection device shown in un-sectioned position, FIG. 4 is a section corresponding to FIG. 3, but with the parts of the coupling shown in disconnection position.

Figure 5:
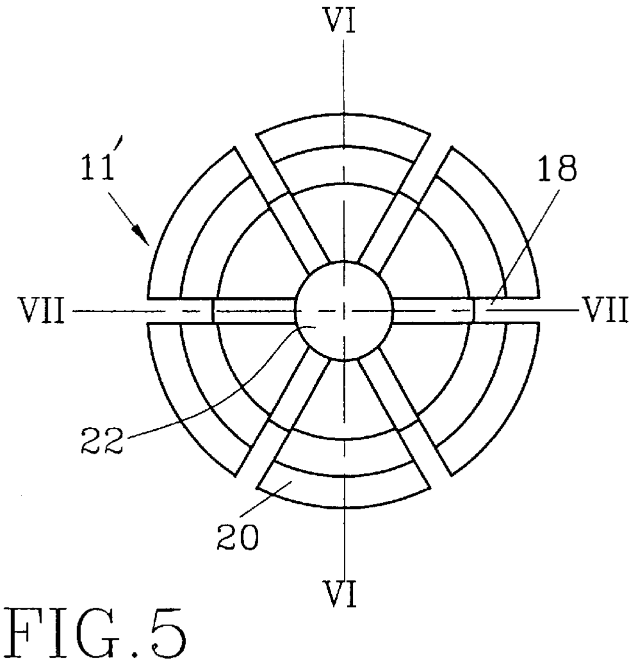
Figure 6:
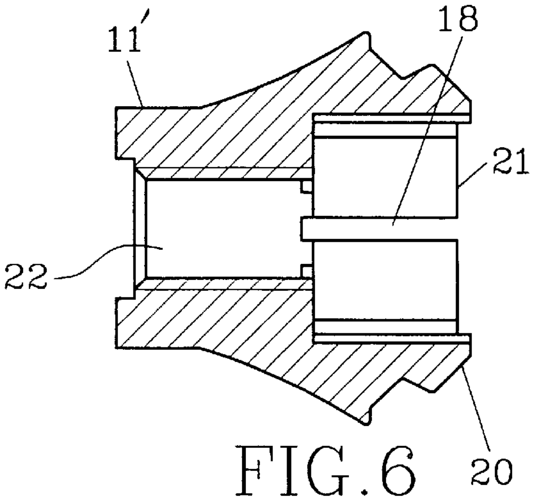
Figure 7:
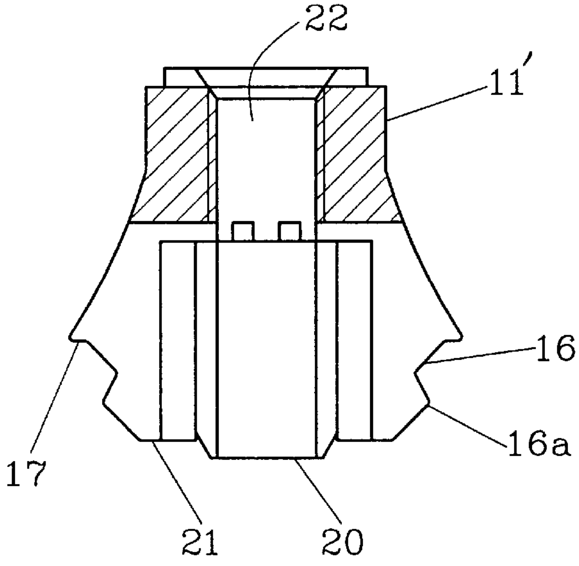

FIGS. 5–7 show in three different views, partially in cross section, a second one of the coupling device, which also forms part of the disconnection device according to the invention.

FIG. 1 shows in cross section a coupling device 1 provided with a disconnection device according to the invention. However, it must be pointed out that the use of the disconnection device is not limited to the embodiment of the coupling device 1 shown, but this does only form an example of a coupling device wherein the disconnection device according to the invention can be included as an essential part.

The coupling device 1, thus shown as an example, incorporates a flange fixture 2 formed as an implant, intended to be inserted by a surgical operation, preferably in the skull bone of the bearer of the hearing aid. The flange fixture or the implant 2 is made as a cylindric body preferably from titanium and near one of its ends it is provided with a radial flange 3, arranged in implanted position to engage the skull bone, such as shown in FIG. 2. In the cylindrical portion of the flange fixture there is provided a threaded blind hole 4, which receives a spacer screw 5 lockable thereto by thread engagement, and by means of which a first coupling part 6, in form of a substantially cup-shaped female part is anchored to the flange fixture 2, said first coupling part having a central through bore, through which extends the shaft of the spacer screw 5. The edge of the screw head retains the first coupling part 6 against the area about the bore in the flange fixture. On its side turned away from the flange fixture 2, the first coupling part 6 is equipped with an axial outwardly tapering annular side wall 7, with annular outer end surface 8 and an inwardly projecting concentric annular bead 9 adjacent the external end surface 8.

The head of the screw 5 thus protrudes upwards inside the space formed by the side wall 7 in the first coupling part, and the head of the screw is covered by a cap-formed covering washer 10, which at its upper portion leaves an annular slot, which extends from the outer end of the conically flaring side wall 7 and beyond its inwardly directed annular bead 9. As the first coupling part 6 is designed as a rigid metal structure made from a high-quality material, it has substantially no resiliency whatsoever, not even at the outer end of its conically flaring side wall 7. The covering washer 10 is preferably manufactured from plastic material, and forms one of the vital members of the disconnection device such as described in detail hereinafter.

The coupling device 1 also incorporates a second coupling part 11, which, as can be seen from FIG. 2, in a proper, not further shown manner, with a shaft portion is connected to a hearing apparatus 12, of a type known per se, and in FIG. 2 is also shown how the implant 2 penetrates the skin 13 and is anchored in the skull bone 14.

In the embodiment illustrated, this second coupling part 11 is made as a male part with a recess 15 arranged in the forward portion thereof and concentric therewith, and being of a size, permitting that the recess is brought down over and encloses the upper portion of the covering washer 10 with clearance.

The second coupling part or the male part 11 at its recess-provided end is equipped with an external, circumferential groove 16 with an engagement surface 16*a* formed at the free edge and adapted to form a seat for the annular bead 9 when the male part 11 is introduced into the annular slot in the first coupling part or the female part 6. The male part 11 is also provided with a radial, circumferential flange 17, which when the annular bead 9 is situated against the engagement surface 16*a* in the groove 16 in the male part engages the end surface 8 on the female part 6. Hereby the annular engagement surfaces between the end surface 8 and the flange 17 and also between the annular bead 9 and the engagement surface 16*a*, form signal transferring surfaces between the first 6 and second 11 coupling parts of the coupling device.

The portion of the second coupling part—the male part 11—having the inner recess 15, is made resilient in order to permit simple snap-in introduction of the male part 11 into the annular slot in the female part 6.

This resiliency can be obtained in different manners, e.g. in that the male part is provided with axial slots 18 in the material around the recess 15, and/or that the entire male part 11 is made in an elastic material, e.g. plastic.

By choosing an elastic material for the male part 11, it thus is possible, with or without slots, to obtain a sufficient resiliency for allowing an easy snapping-in of the male part 11 into the female part 6, thus that a satisfactory signal transferring contact is obtained. Surprisingly this has proven itself to be achievable also when the male part is made of plastic material. For giving a sufficient engagement pressure this coupling must however, be so stiff, that a comparatively big force must be used for disconnection with a pulling force acting in axial direction, and hereby it is also a further drawback that the hearing aid and its sensible vibrator may be damaged.

FIG. 3 shows in a view corresponding to FIG. 1, the coupling device in cross section, whereby the covering washer 10 is shown un-sectioned. From this view in combination with the sectioned illustration according to FIG. 1, it can be seen, that the covering washer 10 has a trough-shaped, substantially cylindrical portion 10*a*, which at its open end has a flanged portion 10*b* with bigger diameter than the through-formed portion 10*a*. On this flanged portion 10*b* there is provided on the upper side at least one, and preferably a number of bosses 19, which, when there are more than one boss, preferably are arranged to be symmetrically distributed along the flange portion 10*b*. These bosses 19 may arbitrarily be radially arranged ridges or point-shaped bosses, whereby however it is convenient that they are smoothly rounded or ramp-shaped in the circumferential direction of the flange portion 10*b*.

In FIG. 4 is shown how the second coupling part 11 has been turned, i.e. has been rotated in its seat formed by the annular wall 7 of the first coupling part, whereby mutually spaced apart, elongated wall portions 20 in the second coupling part 11 during the turning have been situated just in front of the bosses in the covering washer 10, whereby during the turning the boss or bosses 19, urge the second coupling part 11 outwards thus that its circumferential groove 16 is brought out off engagement with the annular bead 9 in the first coupling part 6. At such disconnection, the implant is subjected to equally big forces in the connection direction by the wall portions 20, which press against the bosses 19 on the covering washer 10 and in the opposite direction by the resistance exerted between the annular bead 9 of the first coupling part and the circumferential groove 16 of the second coupling part. In this manner the implant is not subjected to any forces, which might jeopardize or disturb its arresting in the in-operated position. Furthermore it is easy to rotate the second coupling part 11, which is anchored in the hearing apparatus (see FIG. 2).

In FIG. 5 to 7 is shown a somewhat modified embodiment of the second coupling part forming part of the coupling according to Fig.s and here provided with the reference numeral 11'.

In FIG. 5 thus is shown the second coupling part 11', from its coupling side, whereas FIG. 6 shows a cross section along line VI—VI and FIG. 7 a section along line VII—VII in FIG. 5.

As can be seen from these figures the second coupling part in this embodiment constitutes a substantially sleeve formed rotation body with a number of slots 18 and alternating wall portions 20, 21 of different lengths, which at turning of the coupling part 11' in its coupling position, will become situated alternatingly in front of the bosses 19 in the covering washer 10 belonging to the first coupling part 6. When hereby the shorter wall portions 21 are situated just in front of the bosses 19, the coupling parts are in engagement with each other, whereas they as described above are urged apart when the longer wall portions 20 have been turned to positions just in front of the bosses 19.

The coupling part 11' shown in FIGS. 5–7 differ from the embodiment according to FIGS. 1–4 in that it is provided with a threaded coaxial bore 22, for a not shown attachment part of a hearing apparatus.

It also shall be mentioned again that the design of the coupling device shown is not critical for the function of the disconnection device, but other types of the couplings mentioned in the introduction can in similar manner be equipped with the disconnection device according to the invention.

The essential thing is that both coupling parts are mutually rotatable and provided in their surfaces facing each other with portions, which in certain mutual rotational positions allow the parts to be interconnected, whereas they in other mutual rotational positions together have an overall linear length, which exceeds the depth to which the coupling parts can be in engagement with each other.

The invention is neither otherwise limited to the embodiments illustrated in the accompanying drawings and described in connection thereto, but modifications and variations are possible within the scope of the accompanying claims. Thus it is not necessary to make the bosses 19 in a separate covering washer, but they can be arranged directly in the material of the coupling part or the spacer screw. The wall portions of different length and the bosses can in the same manner be arranged in the opposite coupling parts as compared to what has been illustrated in the drawing figures and described in connection thereto.

The invention has been described in connection to a skull bone anchored hearing aid, but the disconnection device according to the invention can of course also be used in other cases with devices or apparatuses of other kinds, which are connected to implants.

We claim:

1. A disconnection device for disconnecting a connection between an implant and a unit connected to the implant, said disconnection device comprising:

a first coupling part having a member portion, said first coupling part comprising a bio-compatible portion attached to said implant; and a second coupling part having a recessed portion adapted to receive the member portion of said first coupling part, wherein snap-in entry of the member portion of said first coupling part into the recessed portion of said second coupling part results in an elastically retained coupling position of said first and second coupling parts having mutual end-to-end contact substantially co-axial with one another and mutually rotatable about a substantially common rotation axis;

said first and second coupling parts forming at least one first mutual rotational position having a total added axial longitudinal measure which leaves a clearance between the member portion of said first coupling part and the recessed portion of said second coupling part when said first and second coupling parts are snapped into the coupling position; and said first and second coupling parts form at least one second mutual rotational position having a total added axial longitudinal measure in which said first and second coupling parts are unsnapped from one another, without exerting an axial influence on said implant, during mutual rotation into said at least one second mutual rotational position.

2. A device as claimed in claim 1 wherein:

said first coupling part member portion further comprises a boss; and said second coupling part further comprises a plurality of axial portions of differing lengths, wherein said boss and said axial portions of shorter length, together are axially shorter than or equal to the axial depth of said second coupling part recess; and said boss and said axial portions of longer length, together are axially longer than the axial depth of said second coupling part recess.

3. The device as claimed in claim 2 wherein said boss is provided on a separate part that is non-rotatably arranged on said first coupling part.

4. The device as claimed in claim 3 wherein said boss comprises ridges extending radially to said substantially common rotation axis.

5. A device as claimed in claim 4 wherein said boss further comprises rounded surfaces in at least one direction of rotation about said common rotation axis.

6. A device as claimed in claim 3 wherein said boss comprises point-shaped raised portions provided along a circumference of said substantially common rotation axis.

7. A device as claimed in claim 6 wherein said boss further comprises rounded surfaces in at least one direction of rotation about said common rotation axis.

8. A device as claimed in claim 3 wherein said unit connected to the implant comprises a vibration exciting hearing aid.

9. The device as claimed in claim 2 wherein said boss further comprises ridges extending radially to said substantially common rotation axis.

10. A device as claimed in claim 9 wherein said boss further comprises rounded surfaces in at least one direction of rotation about said common rotation axis.

11. A device as claimed in claim 2 wherein said boss comprises point-shaped raised portions provided along a circumference of said substantially common rotation axis.

12. A device as claimed in claim 11 wherein said boss further comprises rounded surfaces in at least one direction of rotation about said common rotation axis.

13. A device as claimed in claim 2 wherein said unit connected to the implant comprises a vibration exciting hearing aid.

14. A device as claimed in claim 1 wherein said unit connected to the implant comprises a vibration exciting hearing aid.

15. A disconnection device for disconnecting a connection between an implant and a unit connected to the implant, said disconnection device comprising:

a first coupling part having a member portion, said first coupling part comprising a bio-compatible portion attached to said implant; and a second coupling part having a recessed portion adapted to receive the member portion of said first coupling part, wherein snap-in entry of the member portion of said first coupling part into the recessed portion of said second coupling part results in an elastically retained coupling position of said first and second coupling parts having mutual end-to-end contact substantially co-axial with one another and mutually rotatable about a substantially common rotation axis;

said first and second coupling parts forming at least one first mutual rotational position having a total added axial longitudinal measure which leaves a clearance between the member portion of said first coupling part and the recessed portion of said second coupling part when said first and second coupling parts are snapped into the coupling position; and said first and second coupling parts form at least one second mutual rotational position having a total added axial longitudinal measure in which said first and second coupling parts are unsnapped from one another, without exerting an axial influence on said implant, during mutual rotation into said at least one second mutual rotational position;

said first coupling part member portion further comprises a boss; and said second coupling part further comprises a plurality of axial portions of differing lengths, wherein said boss and said axial portions of shorter length, together are axially shorter than or equal to the axial depth of said second coupling part recess; and said boss and said axial portions of longer length, together are axially longer than the axial depth of said second coupling part recess.

16. A disconnection device for disconnecting a connection between an implant and a unit connected to the implant, said disconnection device comprising:

a first coupling part having a member portion, said first coupling part comprising a bio-compatible portion attached to said implant; and a second coupling part having a recessed portion adapted to receive the member portion of said first coupling part, wherein snap-in means for snap-in entry in a longitudinal direction of the member portion of said first coupling part into the recessed portion of said second coupling part, said snap-in means resulting in an elastically retained coupling position of said first and second coupling parts having mutual end-to-end contact substantially co-axial with one another and mutually rotatable about a substantially common rotation axis;

said first and second coupling parts forming at least one first mutual rotational position having a total added axial measure in said longitudinal direction which leaves a clearance between the member portion of said first coupling part and the recessed portion of said second coupling part when said first and second coupling parts are snapped into the coupling position; and said first and second coupling parts form at least one second mutual rotational position having a total added axial measure in said longitudinal direction in which said first and second coupling parts are unsnapped from one another, without exerting an axial influence on said implant, during mutual rotation into said at least one second mutual rotational position;

said first coupling part member portion further comprises a boss; and said second coupling part further comprises a plurality of axial portions of differing lengths, wherein measured in said longitudinal direction, said boss and said axial portions of shorter length, together are axially shorter than or equal to the axial depth of said second coupling part recess; and measured in said longitudinal direction, said boss and said axial portions of longer length, together are axially longer than the axial depth of said second coupling part recess.

* * * * *